(12) United States Patent
Takachiyo et al.

(10) Patent No.: US 11,344,481 B2
(45) Date of Patent: *May 31, 2022

(54) PIGMENT DISPERSION LIQUID FOR COSMETICS, AND AQUEOUS LIQUID COSMETIC USING SAME

(71) Applicant: MITSUBISHI PENCIL COMPANY, LIMITED, Tokyo (JP)

(72) Inventors: Keiichiro Takachiyo, Fujioka (JP); Satoshi Sakuma, Fujioka (JP)

(73) Assignee: MITSUBISHI PENCIL COMPANY, LIMITED, Tokyo (JP)

( * ) Notice: Subject to any disclaimer, the term of this patent is extended or adjusted under 35 U.S.C. 154(b) by 31 days.

This patent is subject to a terminal disclaimer.

(21) Appl. No.: 16/979,739

(22) PCT Filed: Mar. 8, 2019

(86) PCT No.: PCT/JP2019/009459
§ 371 (c)(1),
(2) Date: Sep. 10, 2020

(87) PCT Pub. No.: WO2019/176801
PCT Pub. Date: Sep. 19, 2019

(65) Prior Publication Data
US 2021/0038487 A1    Feb. 11, 2021

(30) Foreign Application Priority Data

Mar. 12, 2018 (JP) .............................. JP2018-044348

(51) Int. Cl.
| | | |
|---|---|---|
| *A61Q 5/10* | (2006.01) | |
| *A61K 8/04* | (2006.01) | |
| *A61K 8/19* | (2006.01) | |
| *A61K 8/34* | (2006.01) | |
| *A61K 8/81* | (2006.01) | |
| *A61Q 1/10* | (2006.01) | |

(52) U.S. Cl.
CPC ............... *A61K 8/044* (2013.01); *A61K 8/19* (2013.01); *A61K 8/34* (2013.01); *A61K 8/817* (2013.01); *A61K 8/8152* (2013.01); *A61Q 1/10* (2013.01); *A61Q 5/10* (2013.01); *A61K 2800/43* (2013.01); *A61K 2800/59* (2013.01)

(58) Field of Classification Search
CPC ... A61Q 5/10; A61Q 1/02; A61Q 1/10; A61K 8/19; A61K 8/34; A61K 8/817; A61K 2800/43; A61K 2800/432; A61K 8/04; A61K 8/004; A61K 8/8152; A61K 2800/59

USPC ....................................................... 424/70.1
See application file for complete search history.

(56) References Cited

U.S. PATENT DOCUMENTS

| | | | | |
|---|---|---|---|---|
| 2003/0091521 | A1* | 5/2003 | Midha ................. | A61K 8/0241 424/70.1 |
| 2003/0165449 | A1* | 9/2003 | Kaczvinsky, Jr. ...... | A61P 27/02 424/70.1 |
| 2008/0038218 | A1* | 2/2008 | Brun ..................... | A61Q 5/065 424/70.16 |
| 2008/0234392 | A1 | 9/2008 | Ehara et al. | |

FOREIGN PATENT DOCUMENTS

| | | | |
|---|---|---|---|
| JP | H09208436 A | 8/1997 | |
| JP | H10273431 A | 10/1998 | |
| JP | 2001181128 A | 7/2001 | |
| JP | 2005 239626 A * | 9/2005 | ............... A61K 7/13 |
| JP | 2005239626 A | 9/2005 | |
| JP | 4101779 B2 | 3/2008 | |
| JP | 2008308435 A | 12/2008 | |
| JP | 2010260839 A | 11/2010 | |
| JP | 2018058775 A | 4/2018 | |
| WO | 2005072685 A1 | 8/2005 | |
| WO | 2007063902 A1 | 6/2007 | |

OTHER PUBLICATIONS

English transaltion of the Japanese Patent No. JP 2005 239626 A (Feb. 15, 2022).*
International Search Report (with an English translation) and Written Opinion dated Jun. 4, 2019, by the Japan Patent Office as the International Searching Authority for corresponding International Application No. PCT/JP2019/009459. (14 pages).
Extended European Search Report dated Nov. 23, 2021, issued by the European Patent Office in corresponding European Application No. 19766488.1-1112, (6 pages).

* cited by examiner

*Primary Examiner* — Eisa B Elhilo
(74) *Attorney, Agent, or Firm* — Buchanan Ingersoll & Rooney PC

(57) ABSTRACT

Provided are a pigment dispersion liquid for cosmetics having excellent dispersibility of carbon black and aging stability, and an aqueous liquid cosmetic using the same, which is suitable for hair dyes and the like. The pigment dispersion liquid for cosmetics contains, at least, water, a water-soluble organic solvent, carbon black, and a (methacryloyl ethylbetaine/acrylates) copolymer, and a ratio of the water to total solvents is 30 to 95% by mass.

15 Claims, No Drawings

PIGMENT DISPERSION LIQUID FOR COSMETICS, AND AQUEOUS LIQUID COSMETIC USING SAME

TECHNICAL FIELD

The present invention relates to a pigment dispersion liquid for cosmetics having excellent dispersibility of carbon black and aging stability, and an aqueous liquid cosmetic using the same.

BACKGROUND ART

Since pigments have excellent masking properties and color development, many pigment-containing materials have been used as colorants for cosmetics such as temporary hair dyes and makeup cosmetics. In addition, amphoteric polymer resins are often used as resins to be added in cosmetics such as hair dyes.

On the other hand, carbon black is used as a colorant for an aqueous makeup cosmetic or a hair dye. In the eye makeup cosmetic, carbon black is applied to around the eyes, such as eyelids, eyelashes, and eyebrow cosmetics, and is used for adding colors and shades to provide an attractive impression. In hair dyes, carbon black is used for dyeing hair including gray hair. This carbon black has a strong coloring force as a black pigment and is suitably used in aqueous eye makeup cosmetics, hair dyes, and the like, yet carbon black currently has problems such as strong aggregation forces thereby reduced dispersibility and aging stability.

On the other hand, for example, the following related art documents 1) to 5) which refer to dispersibility and aging stability in liquid cosmetics containing a pigment such as carbon black are known.

1) Patent Document 1 describes that carbon black has problems that, in some countries, carbon black cannot be used in cosmetics or the like, as carbon black might be thought to be carcinogenic, and that, despite sufficient color developing properties, it is difficult to wipe out carbon black when removing makeups. Patent Document 1 discloses a temporary hair dye containing an alcohol having 4 or less carbon atoms as main solvent, an N-methacryloylethyl-N, N-dimethylammonium•α-N-methylcarboxybetaine•butyl methacrylate copolymer of an acrylic amphoteric polymer resin as a dispersant, and titanium black as a coloring component. Titanium black is described as an essential component instead of carbon black.

2) Despite the description of Patent Document 1, Patent Document 2 discloses a color hair cosmetic containing water as a main solvent, an acrylic amphoteric polymer resin having a specific structure, an acidic dye, and carbon black. This acrylic amphoteric polymer resin other than the specific structure forms a robust resin coating on the hair, while the poor hair washing performances thereof and strong stiffness have been pointed out as problems. Furthermore, when a dye and a pigment are used in combination, it is known that the viscosity of the cosmetic itself disadvantageously tends to increase through a lapse of time.

3) Furthermore, Patent Document 3, which is a patent filed by the present applicant, discloses that an eyeliner and eyebrow cosmetic is constituted by dispersing carbon black by a copolymer of one selected from the group consisting of acrylic acid, methacrylic acid, and alkyl esters and derivatives thereof with vinyl acetate, a copolymer of vinylpyrrolidone with vinyl acetate, or a copolymer of one or more selected from the group consisting of acrylic acid, methacrylic acid, and alkyl esters or derivatives thereof with octylacrylamide, using water as a main solvent. Furthermore, Patent Document 3 describes that, when carbon black is dispersed using a betaine type alkyl acid amphoteric resin, the stability of the liquid is slightly poor.

4) Patent Document 4 discloses a hair coloring composition which contains water as a main solvent, a branched polyglycerin-modified silicone having a specific structure, a betaine-modified silicone, and a film-forming resin, and which may contain an organic pigment. Also, this patent document indicates, as an example, a hair coloring formulation using the combination of a (methacryloyloxyethyl carboxybetaine/alkyl methacrylate) copolymer, carbon black, Black No. 401 (Acid Black 1: C.I.20470), Violet No. 401 (Acid Violet 43: C.I.60730) and Orange No. 205 (Acid Orange 7, C.I.15510). The patent document does not mention the stability of pigment dispersion.

5) Patent Document 5 discloses a liquid cosmetic containing sepiomelanin, an amphoteric compound, and water. This patent document indicates an example in which this liquid cosmetic contains water as a main solvent and YUKAFORMER™ ((methacryloyloxy ethylcarboxybetaine/alkyl methacrylate) copolymer) used for the dispersion of sepiomelanin. The patent document does not specifically mention the addition of inorganic pigments including carbon black.

CONVENTIONAL ART DOCUMENTS

Patent Documents

Patent Document 1: Japanese Patent Application Laid-Open No. Hei. 9-208436 (Claims, Paragraph [0002], and others)
Patent Document 2: Japanese Patent Application Laid-Open No. Hei. 10-273431 (Claims, Examples, and others)
Patent Document 3: Japanese Patent Application Laid-Open No. 2010-260839 (Claims, Examples, and others)
Patent Document 4: Japanese Patent Application Laid-Open No. 2008-308435 (Claims, Examples, and others)
Patent Document 5: Japanese Patent Application Laid-Open No. 2001-181128 (Claims, Examples, and others)

SUMMARY OF THE INVENTION

Problems to be Solved by the Invention

The present invention is to solve the above problems, and an object thereof is to provide a pigment dispersion liquid for cosmetics having excellent dispersibility of carbon black and aging stability, and an aqueous liquid cosmetic using the same, which is suitable for hair dyes and the like.

Means to Solve Problems

As a result of dedicated study on the above problems and the like, the present inventors found that, by incorporating at least water, a water-soluble organic solvent, carbon black, and a specific component, and setting a ratio of the water to total solvents to be within a specific range, the aforementioned pigment dispersion liquid for cosmetics and aqueous liquid cosmetic using the same, which is suitable for hair dyes and the like, are obtained, and completed the present invention.

Specifically, the pigment dispersion liquid for cosmetics of the present invention includes, at least, water, a water-soluble organic solvent, carbon black, and a (methacryloyl ethylbetaine/acrylates) copolymer, and a ratio of the water to total solvents is 30 to 95% by mass.

The water-soluble organic solvent is preferably a lower alcohol having 5 or less carbon atoms.

The lower alcohol is preferably ethanol.

The aqueous liquid cosmetic of the present invention contains the pigment dispersion liquid for cosmetics described above.

The aqueous liquid cosmetic preferably has a ratio of the water to total solvents 30 to 95% by mass.

In the aqueous liquid cosmetic, the lower alcohol having 5 or less carbon atoms is preferably contained besides the water.

The lower alcohol of the aqueous liquid cosmetic is preferably ethanol.

Effects of the Invention

The present invention provides a pigment dispersion liquid for cosmetics having excellent dispersibility of carbon black and aging stability, and an aqueous liquid cosmetic using the same, which is suitable for hair dyes and the like.

DESCRIPTION OF EMBODIMENTS

Hereinafter, embodiments of the present invention will be described in detail.

The pigment dispersion liquid for cosmetics of the present invention contains, at least, water, a water-soluble organic solvent, carbon black, and a (methacryloyl ethylbetaine/acrylates) copolymer, and a ratio of the water to total solvents is 30 to 95% by mass.

The carbon black used in the present invention is used as a colorant for an eye makeup cosmetic or a hair dye. Carbon black is not particularly limited as long as the carbon black is normally used as a colorant for a black-color liquid cosmetic, and various types of carbon black can be used.

An aqueous dispersion liquid containing carbon black needs a long dispersion time due to strong aggregation forces, and reduced productivity and aging stability in the manufacture of the dispersion liquid, yet these problems will be overcome by preparing a dispersion liquid having with the blending characteristics according to the present invention.

The content of carbon black used is preferably 1 to 32% by mass, more preferably 2 to 25% by mass, based on the total amount of the pigment dispersion liquid for cosmetics, from the perspective of stability after dispersion and convenience in the manufacture of the cosmetics.

Setting the content of carbon black to 1% by mass or greater leads to excellent productivity and coloration properties when the pigment dispersion liquid is added to cosmetics. Moreover, when the content is set to 32% by mass or less, that leads to even better dispersibility and aging stability.

The water-soluble organic solvent for the present invention is used as a solvent for the pigment dispersion liquid for cosmetics, and examples thereof include lower alcohols having 5 or less carbon atoms. A specific example of the water-soluble organic solvent is at least one (alone or a mixture of two or more) of: methyl alcohol (methanol), ethyl alcohol (ethanol), n-propyl alcohol, isopropyl alcohol, n-butyl alcohol, sec-butyl alcohol, tert-butyl alcohol, isobutyl alcohol, pentyl alcohol, ethylene glycol, propylene glycol, and the like.

In particular, it is desired to use ethyl alcohol (ethanol), from the perspective of safety, handleability, and the like.

The content of the water-soluble organic solvent used is preferably 1.0 to 60.0% by mass, more preferably 5.0 to 30.0% by mass based on the total amount of the pigment dispersion liquid for cosmetics, from the perspective of stability, in a dissolved state, of the (methacryloyl ethylbetaine/acrylates) copolymer which will be described below, and, additionally, carbon black dispersion stability, especially, stability at low temperatures.

By setting the content of the water-soluble organic solvent to 1.0% by mass or greater, it is possible to achieve the effect of preventing the solvent from freezing at low temperatures and an antiseptic effect though slight. On the other hand, by setting the content to 60.0% by mass or less, the stability in a dissolved state of the (methacryloyl ethylbetaine/acrylates) copolymer is further improved as described below.

The (methacryloyl ethylbetaine/acrylates) copolymer for the present invention is a component which improves the dispersibility of carbon black and the aging stability when used to prepare a dispersion liquid.

This (methacryloyl ethylbetaine/acrylates) copolymer is a copolymer of two or more monomers composed of acrylic acid, methacrylic acid, or a simple ester thereof and methacryloyl ethylbetaine, which is generally called N-methacryloyloxyethyl-N,N-dimethylammonium-α-N-methylcarboxybetaine/alkyl mathacrylate copolymer, and has a betaine unit in the polymer structure, and a polymer with the betaine unit exhibits specific behaviors different from behaviors of the other ionic polymers.

The (methacryloyl ethylbetaine/acrylates) copolymer is a component that has been heretofore used as a film-forming agent or a hairstyling agent, but, in the case of the present invention, is a component that provides novel applications as a component which improves the dispersibility of carbon black and the aging stability when used to prepare a dispersion liquid.

The (methacryloyl ethylbetaine/acrylates) copolymer that can be used include, RAM Resin-1000 (manufactured by Osaka Organic Chemical Industry Ltd.) and Plascize L-440 (manufactured by GOO CHEMICAL CO., LTD.), or the like among commercially available products.

The content of the (methacryloyl ethylbetaine/acrylates) copolymer used is preferably 3.0 to 15.0% by mass, more preferably 5.0 to 10.0% by mass, in terms of solid content, based on the total amount of the pigment dispersion liquid for cosmetics, from the perspective of achieving excellent dispersibility of carbon black and excellent aging stability when the (methacryloyl ethylbetaine/acrylates) copolymer is used to prepare a dispersion liquid.

By setting the content of the (methacryloyl ethylbetaine/acrylates) copolymer to 3.0% by mass or more, the dispersion state of carbon black is stabilized, and the binding of the pigment or the like when blended into a cosmetic is improved. On the other hand, by setting the content to 15.0% by mass or less, the increase in viscosity is suppressed so that the convenience in the manufacture of the cosmetic is further improved.

In the present invention, the blending ratio between carbon black and the (methacryloyl ethylbetaine/acrylates) copolymer used is desirably set to a mass ratio of carbon black to the (methacryloyl ethylbetaine/acrylates) copolymer of 1:1 to 4:1, and is particularly preferably 2:1 to 4:1.

By setting the ratio to 1:1 to 4:1, a pigment dispersion liquid for cosmetics achieving both excellent dispersibility of carbon black and excellent aging stability can be obtained.

Water used as a solvent for the present invention can be distilled water, ion exchanged water, purified water, pure water, ultrapure water, or the like, and a ratio of water to total solvents (a total of water and water-soluble organic solvent) must be 30 to 95% by mass (0.30 to 0.95), and is preferably 60 to 95% by mass.

When the ratio of water to total solvents is less than 30% by mass (0.30), the aging stability becomes unstable, and carbon black cannot be dispersed. On the other hand, when the ratio exceeds 95% by mass (0.95), no pigment dispersion liquid for cosmetics can be manufactured due to the solvent, other than water, originally contained in each of the components.

The pigment dispersion liquid for cosmetics of the present invention contains the water-soluble organic solvent, carbon black, (methacryloyl ethylbetaine/acrylates) copolymer, and water as described above, but a pH modifier, a surfactant, a viscosity modifier, a chelating agent, and the like can be appropriately used according to need, from the perspective of further improvement in dispersibility and stability, in a dissolved state, of each of the components.

Furthermore, the pigment dispersion liquid for cosmetics of the present invention can be prepared by blending the water-soluble organic solvent, carbon black, (methacryloyl ethylbetaine/acrylates) copolymer, water, and other components as described above within the content ranges as described above, and homogeneously stirring and mixing the components.

For example, the pigment dispersion liquid for cosmetics can be prepared by stirring carbon black, a water-soluble solvent, and a solvent such as water with a general purpose disperser or the like until homogeneous, mixing a (methacryloyl ethylbetaine/acrylates) copolymer therewith, and then further stirring the components with a disperser or the like using a homomixer or the like until homogeneous.

The thus-configured pigment dispersion liquid for cosmetics of the present invention can solve the problems of the long dispersion time needed for carbon black as a black pigment in the dispersion liquid and low aging stability, and provides a pigment dispersion liquid for cosmetics having excellent dispersibility of carbon black and aging stability.

The obtained pigment dispersion liquid for cosmetics is suitably used in applications of cosmetics containing carbon black, and preferred examples thereof include eye makeup cosmetics, scalp hair cosmetics, and nail cosmetics. For example, there are indicated eye makeup cosmetics such as eye shadows, eyeliner cosmetics, eyebrow cosmetics, and mascaras, rinses, conditioners, hair colors, hair restorers, nail colors, treatment nails, and various gel nails. In addition, the form of the product is not particularly limited, but the product can be applied to aqueous products such as liquids, emulsions, creams, pastes, gels, mousses, and sprays, because it is a dispersion liquid (aqueous).

In particular, the pigment dispersion liquid for cosmetics of the present invention is preferably used in aqueous liquid cosmetics such as hair dyes, eye makeup cosmetics (including eyeliner cosmetics, mascaras, and eye shadows), and aqueous nail colors due to the dispersion characteristics thereof.

As a specific embodiment of the aqueous liquid cosmetic of the present invention, the use thereof in a hair dye will be described below.

Examples of the hair dye that can be used include hair dyes containing, at least, the pigment dispersion liquid for cosmetics containing carbon black described above and general purpose hair dye components such as a resin, a lower alcohol, a hair dyeing aid, a pH modifier, and water. The hair dye can further contain a colorant other than carbon black described above, according to the color variation of the hair dye, as needed The content of the pigment dispersion liquid for cosmetics containing carbon black described above is preferably 0.5 to 30.0% by mass, more preferably 1.0 to 25.0% by mass based on the total amount of the hair dye, from the perspective of hair dyeing effect, solubility, storage stability, and the like.

Colorants other than carbon black, which can be used are dyes generally used in hair dyes, and examples thereof include inorganic pigments such as black titanium oxide, yellow iron oxide, black iron oxide, red iron oxide, ultramarine blue, iron blue, chromium oxide, chromium hydroxide, carmine, and shikonin, and organic pigments such as barium, calcium, zirconium or aluminum lake pigments of water-soluble dyes such as Red No. 2 (Acid Red No. 27: C.I.16185), Red No. 3 (Acid Red 51: C.I.45430), Red No. 102 (Acid Red 18: C.I.16255), Red No. 104 (1) (Acid Red 92: C.I.45410), Red No. 105 (1) (Acid Red 94: C.I.45440), Red No. 106 (Acid Red 52: C.I.45100), Red No. 227 (Acid Red 33: C.I.17200), Red No. 230 (1) and Red No. 230 (2) (both Acid Red 87: C.I.45380), Red No. 231 (Acid Red 92: C.I.45410), Red No. 232 (Acid Red 94: C.I.45440), Yellow No. 4 (Acid Yellow No. 23: C.I.19140), Yellow No. 5 (Food Yellow 3: C.I.15985), Yellow No. 202 (1) and Yellow No. 202 (2) (both Acid Yellow 73: C.I.45350), Yellow No. 203 (Acid Yellow 3: C.I.47005), Green No. 3 (Food Green: C.I.42053), Green No. 201 (Acid Green No. 25: C.I.61570), Green No. 204 (Solvent Green 7: C.I.59040), Green No. 205 (Acid Green 5: C.I.42095), Blue No. 1 (Food Blue No. 2: C.I.42090), Blue No. 2 (Acid Blue 74: C.I.73015), Blue No. 202 (Acid Blue 5: C.I.42052), Blue No. 205 (Acid Blue 9: C.I.42090, Orange No. 205 (Acid Orange 7: C.I.15510, Orange No. 207 (Acid Red 95: C.I.45425, and Brown No. 201 (Acid Orange 24: C.I.20170), Red No. 201 (Pigment Red 57-1: C.I.15850), Red No. 202 (Pigment Red 57: C.I.15850), Red No. 203 (Pigment Red 53: C.I.15585), Red No. 204 (Pigment Red 53 (Ba): C.I.15585), Red No. 205 (Pigment Red 49 (Na): C.I.15630), Red No. 206 (Pigment Red 49 (Ca): C.I.15630), Red No. 207 (Pigment Red 49 (Ba): C.I.15630), Red No. 208 (Pigment Red 49 (Sr): C.I.15630), Red No. 215 (Solvent Red 49: C.I.45170), Red No. 218 (Solvent Red 48: C.I.45410), Red No. 219 (Pigment Red 64: C.I.15800), Red No. 220 (Pigment Red 63 (Ca): C.I.15880), Red No. 221 (Pigment Red 3: C.I.12120), Red No. 223 (Solvent Red 43: C.I.45380), Red No. 225 (Solvent Red No. 23: C.I.26100), Red No. 226 (Vat Red 1: C.I.73360), Yellow No. 201 (Acid Yellow 73: C.I.45350), Yellow No. 204 (Solvent Yellow 33: C.I.47000), Yellow No. 205 (Pigment Yellow 12: C.I.21090), Green No. 202 (Solvent Green 3: C.I.61565), Blue No. 201 (Vat Blue 1: C.I.73000), Blue No. 204 (Vat Blue 6: C.I.69825), Blue No. 404 (Pigment Blue 15: C.I.74160, Orange No. 201 (Solvent Red 72: C.I.45370, Orange No. 203 (Pigment Orange 5: C.I.12075, Orange No. 204 (Pigment Orange 13: C.I.21110, Orange No. 206 (Solvent Red 73: C.I.45425, Orange No. 401 (Pigment Orange 1: C.I.11725, Orange No. 402 (Acid Orange 20: C.I.14600, Orange No. 403 (Solvent Orange 2: C.I.12100) Black No. 401 (Acid Black 1: C.I.20470), and Violet No. 201 (Solvent Violet 13: C.I.60725). At least one of these colorants can be used.

When these colorants are used, colorants are to be used in an amount 1.0 to 25.0% by mass based on the total amount of the hair dye, from the perspective of hair dyeing effect, solubility, storage stability, and the like.

The resin that can be used is, for example, a resin having water resistance or a resin having a film forming property, and an example thereof is at least one of (methacryloyloxy ethylcarboxybetaine/alkyl methacrylate) copolymers, (octylacrylamide/hydroxypropyl acrylate/butylaminoethyl methacrylate) copolymers, (hydroxyethyl acrylate/butyl acrylate/methoxyethyl acrylate) copolymers, N-methacryloylethyl-N,N-diemethylammonium•α-N-methylcarboxybetaine•butyl methacrylate copolymers, and (methacryloyl ethylbetaine/acrylates) copolymers.

These resins are preferably used in an amount 0.1 to 10.0%, preferably 0.5 to 5.0%, in terms of solid content, based on the total amount of the hair dye, from the perspective of water resistance, texture after application to the hair, coatability, and the like.

The lower alcohol that can be used can be preferably used from the perspective of low temperature stability, drying property, low irritation, and the like. Examples of the lower alcohol used include lower alcohols having 5 or less carbon atoms. A specific example of the lower alcohol is at least one (alone or as a mixture of two or more) of methyl alcohol (methanol), ethyl alcohol (ethanol), n-propyl alcohol, iso-propyl alcohol, n-butyl alcohol, sec-butyl alcohol, tert-butyl alcohol, isobutyl alcohol, pentyl alcohol, and the like.

In particular, it is desired to use ethyl alcohol (ethanol), from the perspective of safety, handleability, and the like.

These lower alcohols are preferably used in an amount of 10 to 80% by mass, more preferably 15 to 70% by mass, particularly preferably 15 to 65% by mass, based on the total amount of the hair dye.

The hair dyeing aid that can be used is used for further improvement of the hair dyeing effect, and is, for example, at least one of benzyl alcohol, phenylethyl alcohol, phenoxy ethanol, propylene carbonate, propylene glycol, ethoxydiglycol, N-methylpyrrolidone, N-methyl-2 pyrrolidone, and the like.

These hair dyeing aids are preferably used in an amount 2.0 to 20.0%, more preferably 5.0 to 15.0%, particularly preferably 3.0 to 5.0% based on the total amount of the hair dye, from the perspective of further hair dyeing effect.

The pH modifier that can be used is for improving coloration properties, preventing skin irritation, and preventing skin dyeing troubles, and the pH of the hair dye is adjusted to preferably 2 to 5, and more preferably 3.5 to 5.0 by this pH modifier.

Examples of the pH modifier that can be used include organic acids and inorganic acids such as formic acid, acetic acid, lactic acid, tartaric acid, malic acid, citric acid, and glycolic acid, or salts thereof. In some cases, an alkali such as triethanolamine can be used.

The balance of the hair dye is adjusted with water (purified water, distilled water, ion exchanged water, pure water, tap water, etc.).

As the water content, the ratio of water to total solvents (a total of water and water-soluble organic solvent) is set preferably within the range 30 to 95% by mass (0.30 to 0.95), more preferably within the range 30 to 80% by mass.

If the ratio of water to total solvents is less than 30% by mass (0.30), the aging stability will be poor, and the stability, in a dissolved state, of the water-soluble component when added will be worsened. On the other hand, if the ratio exceeds 95% by mass (0.95), the possibility of inferior antimicrobial properties will be increased.

The thus-configured hair dye contains, at least, the pigment dispersion liquid for cosmetics containing carbon black, resin, lower alcohol, hair dyeing aid, and pH modifier as described above. However, the hair dye can appropriately contain other materials within ranges that do not impair the effects of the present invention, for example, thickeners, various surfactants, preservatives, UV absorbers, antioxidants, anti-reduction agents, chelating agents, oily components, perfumes, and animal/plant extracts.

Examples of the thickener that can be used include cellulose thickeners such as hydroxyethyl cellulose, hydroxypropylmethyl cellulose, stearoxyhydroxypropylmethyl cellulose, hydroxypropylguar hydroxypropyltrimonium chloride, and cationized cellulose in which a cationic functional group is added to cellulose, resin thickeners such as polyvinyl alcohol and acrylic acid, and clay thickeners such as bentonite, from the perspective of coatability, storage stability, suppression of pigment sedimentation, and the like.

When the hair dye is applied to a container using sliver, the viscosity of the hair dye at 25° C. (cone plate viscometer: 50 rpm) is 1.0 to 200 mPa·s, for proper viscosity, dye dissolution stability, imparting smoothness, suppleness, and moist feel to the hair to improve the touch, improving water resistance, further improving usability and coatability when the hair dye is used in an applicator, and application to the hair.

Similarly, when the hair dye is applied to a container using a valve, the viscosity of the hair dye at 25° C. (cone plate viscometer: 50 rpm) is desirably 1.0 to 100 mPa·s.

Furthermore, when the hair dye is applied to a mascara-shaped container, the viscosity of the hair dye at 25° C. (cone plate viscometer: 50 rpm) is desirably 10 to 200 mPa·s, more desirably 1.0 to 50 mPa·s, further desirably 1.0 to 10.0 mPa·s.

The viscosity range (1.0 to 200 mPa·s) can be modified by suitably modifying the amounts of the components used, the type of the thickener preferably used, as described above, and the amount thereof, and the like.

By setting the viscosity of the hair dye to 1.0 mPa·s or greater, liquid leakage from a container or the like is unlikely to occur. Further, the hair dye is unlikely to adhere to the scalp, and does not soil the clothing. On the other hand, by setting the viscosity to 200 mPa·s or less, a user easily controls the amount of the liquid entangled with the applicator such as a brush, and can evenly coat the hair dye to the hair.

The hair dye of the present embodiment can be prepared by an ordinary method, and a hair dye having preferable viscosity range and pH range as described above can be manufactured by blending components such as the pigment dispersion liquid for cosmetics containing carbon black, resin, lower alcohol, hair dyeing aid, pH modifier and water as described above, within the content ranges as described above and further homogeneously stirring and mixing components with a suitable kneader or the like.

For example, the target hair dye can be prepared by stirring a resin, an alcohol phase such as a lower alcohol, and a colorant containing carbon black, and an aqueous phase such as water with a general purpose disperser or the like until homogeneous, mixing the alcohol phase and the aqueous phase, further adding a pH modifier, a thickener, and the like, stirring the components with a disperser or the like until homogeneous, and then stirring the components with a homomixer or the like.

When the thus-configured hair dye of the present embodiment is used, a general purpose hair applicator can be used. The shape, structure, and the like of the hair applicator used are not particularly limited, and examples thereof include an applicator provided with a knock-type valve device, a hair mascara-type applicator, a tube-type applicator, and an applicator provided with a piston pressing mechanism.

The thus-configured hair dye of the present embodiment contains, at least, the pigment dispersion liquid for cosmetics containing carbon black, resin, lower alcohol, hair dyeing aid, pH modifier, and water as described above, and thus has excellent dispersibility of carbon black as a black pigment and aging stability. Therefore, a hair dye that ensures stable dispersion of the coloring component thereof, has excellent storage stability, water resistance, usability, coatability, low temperature stability, drying property, low irritation, and the like can be obtained.

EXAMPLE

Next, the present invention will be described in further detail with reference to examples and comparative examples, although the present invention is not limited to the following examples and the like.

Example 1 to 12 and Comparative Example 1 to 4: Preparation of Pigment Dispersion Liquid for Cosmetics A pigment dispersion liquid for cosmetics was prepared by dispersing a pigment with each of the blending formulations indicated in Table 1 below in a bead mill.

For each of the obtained pigment dispersion liquids for cosmetics of Example 1 to 12 and Comparative Example 1 to 4, the particle diameter and aging stability were evaluated by the following evaluation method.

These evaluation results are indicated in Table 1 below.

Measurement of Particle Diameter of Pigment Dispersion Liquid for Cosmetics

For each of the obtained pigment dispersion liquids for cosmetics, the particle diameter (histogram average particle diameter based on the scattered light intensity distribution: D50) was measured at 25° C. with a particle counter [FPAR-1000 (manufactured by Otsuka Electronics Co., Ltd.)].

Aging Stability: 50° C., After 1 Month

Each of the obtained pigment dispersion liquids for cosmetics was contained in a glass storage container with a lid, allowed to stand at 50° C. for 1 month, and then evaluated on the basis of the following evaluation criteria.
Evaluation Criteria:
A: The particle diameter is 200 nm or less, and the pigment dispersion liquid is stable (dispersion is homogeneous and stable with no sedimentation or aggregation).
B: The particle diameter exceeds 200 nm at the initial stage. Or, the particle diameter increases over time.
C: Gelated.

TABLE 1

| | | | | Example | | | | | (Total 100% by mass) |
|---|---|---|---|---|---|---|---|---|---|
| | 1 | 2 | 3 | 4 | 5 | 6 | 7 | 8 | 9 |
| Water (Purified water) | 54.10 | 54.10 | 54.10 | 54.10 | 54.10 | 77.09 | 66.68 | 55.76 | 54.09 |
| Ethanol | 27.20 | 4.20 | 4.20 | 4.20 | 4.20 | 4.16 | 8.33 | 28.00 | 27.16 |
| Propanol | | 23.00 | | | | | | | |
| Propylene glycol | | | 23.00 | | | | | | |
| Ethylene glycol | | | | 23.00 | | | | | |
| Isopropanol | | | | | 23.00 | | | | |
| Carbon black | 12.50 | 12.50 | 12.50 | 12.50 | 12.50 | 12.50 | 12.50 | 12.50 | 12.50 |
| 70% Pigment Yellow 1 (C.I. 11680: Yellow No. 401) Barium sulfate | | | | | | | | | |
| (Methacryloyl ethylbetaine/ acrylates) copolymer | 6.20 | 6.20 | 6.20 | 6.20 | 6.20 | 6.25 | 12.49 | 3.74 | 6.25 |
| Polyquaternium-55 *1 | | | | | | | | | |
| (VP/Acryl DMAPA) copolymer *2 | | | | | | | | | |
| water/total solvents | 0.67 | 0.67 | 0.67 | 0.67 | 0.67 | 0.95 | 0.89 | 0.67 | 0.67 |
| Particle diameter [nm] | 73 | 162 | 183 | 174 | 180 | 176 | 186 | 166 | 140 |
| Aging stability [50° C., after 1 month, Upper row: particle diameter (nm), Lower row: evaluation] | 92 A | 159 A | 185 A | 169 A | 182 A | 180 A | 182 A | 174 A | 153 A |

| | | Example | | | Comparative Example | | (Total 100% by mass) |
|---|---|---|---|---|---|---|---|
| | 10 | 11 | 12 | 1 | 2 | 3 | 4 |
| Water (Purified water) | 24.29 | 55.30 | 40.50 | 14.56 | 44.09 | 60.00 | 60.00 |
| Ethanol | 56.96 | 37.20 | 22.00 | 69.20 | 37.16 | 30.00 | 30.00 |
| Propanol | | | | | | | |
| Propylene glycol | | | | | | | |
| Ethylene glycol | | | | | | | |
| Isopropanol | | | | | | | |
| Carbon black | 12.50 | 2.50 | 30.00 | 12.50 | | 8.00 | 8.00 |
| 70% Pigment Yellow 1 (C.I. 11680: Yellow No. 401) Barium sulfate | | | | | 12.50 | | |
| (Methacryloyl ethylbetaine/ acrylates) copolymer | 6.25 | 5.00 | 7.50 | 3.74 | 6.25 | | |

TABLE 1-continued

| | | | | | | | |
|---|---|---|---|---|---|---|---|
| Polyquaternium-55 *1 | | | | | | 2.00 | |
| (VP/Acryl DMAPA) copolymer *2 | | | | | | | 2.00 |
| water/total solvents | 0.30 | 0.60 | 0.65 | 0.17 | 0.54 | 0.67 | 0.67 |
| Particle diameter [nm] | 153 | 95 | 188 | 254 | gelation | gelation | gelation |
| Aging stability [50° C., after 1 month, Upper row: particle diameter (nm), Lower row: evaluation] | 148<br>A | 97<br>A | 182<br>A | 262<br>B | gelation<br>C | gelation<br>C | gelation<br>C |

*1: Polymer of quaternary ammonium salt obtained from the reaction of vinylpyrrolidone, dimethylaminopropyl methacrylamide, with (methacrylamido)propyl lauryldimmonium chloride
*2: Copolymer of vinylpyrrolidone with dimethylaminopropyl acrylamide or dimethylaminopropyl methacrylamide As is clear from the results in Table 1 above, Examples 1 to 12 of the present invention were confirmed to be satisfactory in particle diameters and were excellent in both dispersibility and aging stability, as compared with Comparative Examples 1 to 4 out of scope of the present invention.

Example 13 to 18 and Comparative Example 5: Preparation of Hair Dye

Using each of the pigment dispersion liquids for cosmetics obtained above, a hair dye was prepared by stirring components with each of the blending formulations indicated in Table 2 below.

For each of the obtained hair dyes, the particle diameter and aging stability were measured by the measurement method described above, and the viscosity, pH, dyeing property, and drying property were evaluated according to the following evaluation methods.

These results are indicated in Table 2 below.

Method for Measuring Viscosity

For each of the hair dyes of Example 13 to 18 and Comparative Example 5 obtained, the viscosity at 25° C. (viscosity measured with a cone plate viscometer: 50 rpm was measured by the method described above.

Method for Measuring pH

For each of the hair dyes of Example 1 to 18 and Comparative Example 5 obtained by the method described above, the pH at 25° C. was measured with a glass electrode pH meter.

Method for Evaluating Dyeing Property

Each of the obtained hair dyes (0.2 g) was applied to a human hair bundle (10 cm, 1 g) using a brush, and then dried at room temperature, and sensory evaluation of the dyeing state was made based on the following evaluation criteria.
Evaluation Criteria:
A: Dyed well, and dyeing is maintained.
B: Not dyed well, but not uneven in color.
C: Dyed poorly, or uneven in color.

Method for Evaluating Drying Property

Each of the obtained hair dyes was applied to a human hair bundle (10 cm, 1 g) using a brush, and then dried at room temperature, and evaluated based on the following evaluation criteria.
Evaluation Criteria:
A: After 5 minutes, no color migration occurs.
B: Color migration occurs even after a lapse of 5 minutes.

TABLE 2

| | Example | | | | | | (Total 100% by mass) Comparative Example |
|---|---|---|---|---|---|---|---|
| | 13 | 14 | 15 | 16 | 17 | 18 | 5 |
| Water (Purified water) | 52.36 | 27.00 | 71.00 | 17.36 | 82.36 | 49.26 | 52.36 |
| Ethanol | 35.90 | 61.26 | 17.26 | 70.9 | 5.9 | 35.9 | 35.9 |
| Example 1 (dispersion liquid of pigment) | 7.00 | 7.00 | 7.00 | 7.00 | 7.00 | 7.00 | |
| Comparative Example 1 (dispersion liquid of pigment) | | | | | | | 7.00 |
| Acid Black 1 (C.I. 20470: Black No. 401) | | | | | | 0.40 | |
| Acid Violet 43 (C.I. 60730: Violet No. 401) | | | | | | 0.30 | |
| Acid Orange 7 (C.I. 15510: Orange No. 205) | | | | | | 0.40 | |
| (Methacryloyl ethylbetaine/ acrylates) copolymer | 1.20 | 1.20 | 1.20 | 1.20 | 1.20 | 3.20 | 1.20 |
| Propylene glycol | 3.00 | 3.00 | 3.00 | 3.00 | 3.00 | 3.00 | 3.00 |
| Lactic acid | 0.54 | 0.54 | 0.54 | 0.54 | 0.54 | 0.54 | 0.54 |
| water/total solvents | 0.59 | 0.31 | 0.80 | 0.20 | 0.93 | 0.58 | 0.59 |
| Viscosity (25° C., mPa · s) | 5.7 | 5.8 | 5.6 | 5.7 | 5.9 | 4.7 | 6.1 |
| pH (25° C.) | 4.6 | 4.9 | 4.7 | 4.8 | 4.7 | 6.5 | 5.0 |
| Particle diameter [nm] | 184 | 192 | 202 | 188 | 182 | 187 | 301 |
| Aging stability [50° C., after 1 month, Upper row: particle diameter (nm), Lower row: evaluation] | 188<br>A | 182<br>A | 198<br>A | 245<br>A | 186<br>A | 192<br>A | 324<br>B |

TABLE 2-continued

| Dyeing property | A | A | A | A | A | A | A |
|---|---|---|---|---|---|---|---|
| Drying property | A | A | A | A | B | A | A |

As is clear from the results shown in Table 2 above, each of the hair dyes of Example 13 to 18 was confirmed to be satisfactory in viscosity and pH, to be satisfactory in particle diameter and excellent in both of dispersibility of carbon black and aging stability, and also to be able to achieve both excellent dyeing property and excellent drying property, as a hair dye, as compared with the hair dye of Comparative Example 5.

INDUSTRIAL APPLICABILITY

Obtained are a pigment dispersion liquid for cosmetics having excellent dispersibility of carbon black and aging stability, and an aqueous liquid cosmetic using the same, which is suitable for hair dyes and the like.

The invention claimed is:

1. A pigment dispersion liquid for cosmetics comprising, at least, water, a water-soluble organic solvent, carbon black, and a (methacryloyl ethylbetaine/acrylates) copolymer, wherein a ratio of the water to total solvents is 30 to 95% by mass.

2. The pigment dispersion liquid for cosmetics described in claim 1, wherein the water-soluble organic solvent is a lower alcohol having 5 or less carbon atoms.

3. The pigment dispersion liquid for cosmetics described in claim 2, wherein the lower alcohol is ethanol.

4. An aqueous liquid cosmetic comprising the pigment dispersion liquid for cosmetics described in claim 1.

5. The aqueous liquid cosmetic described in claim 4, wherein a ratio of the water to total solvents of the aqueous liquid cosmetic is 30 to 95% by mass.

6. The aqueous liquid cosmetic described in claim 5, wherein a lower alcohol having 5 or less carbon atoms is contained besides the water.

7. The aqueous liquid cosmetic described in claim 6, wherein the lower alcohol is ethanol.

8. The aqueous liquid cosmetic comprising the pigment dispersion liquid for cosmetics described in claim 2.

9. The aqueous liquid cosmetic described in claim 8, wherein a ratio of the water to total solvents of the aqueous liquid cosmetic is 30 to 95% by mass.

10. The aqueous liquid cosmetic described in claim 9, wherein a lower alcohol having 5 or less carbon atoms is contained besides the water.

11. The aqueous liquid cosmetic described in claim 10, wherein the lower alcohol is ethanol.

12. The aqueous liquid cosmetic comprising the pigment dispersion liquid for cosmetics described in claim 3.

13. The aqueous liquid cosmetic described in claim 12, wherein a ratio of the water to total solvents of the aqueous liquid cosmetic is 30 to 95% by mass.

14. The aqueous liquid cosmetic described in claim 13, wherein a lower alcohol having 5 or less carbon atoms is contained besides the water.

15. The aqueous liquid cosmetic described in claim 14, wherein the lower alcohol is ethanol.

* * * * *